(12) United States Patent
Jackson

(10) Patent No.: US 6,713,470 B2
(45) Date of Patent: Mar. 30, 2004

(54) METHOD OF TREATMENT

(75) Inventor: Karen Jackson, Sheffield (GB)

(73) Assignee: ML Laboratories PLC, London (GB)

( * ) Notice: Subject to any disclaimer, the term of this patent is extended or adjusted under 35 U.S.C. 154(b) by 0 days.

(21) Appl. No.: 10/349,431

(22) Filed: Jan. 22, 2003

(65) Prior Publication Data

US 2003/0153592 A1 Aug. 14, 2003

Related U.S. Application Data

(63) Continuation-in-part of application No. 10/108,659, filed on Mar. 27, 2002, which is a continuation-in-part of application No. 10/053,962, filed on Jan. 22, 2002.

(30) Foreign Application Priority Data

Jan. 22, 2002 (GB) .............................................. 0201367

(51) Int. Cl.$^7$ .............................................. A61R 31/55
(52) U.S. Cl. ................................................. 514/211.05
(58) Field of Search ..................................... 514/211.05

(56) References Cited

U.S. PATENT DOCUMENTS

| 5,153,191 A | 10/1992 | Woodruff ..................... 514/221 |
| 5,550,126 A | * 8/1996 | Horwell et al. .......... 514/237.5 |

FOREIGN PATENT DOCUMENTS

| EP | 0517412 | * 12/1992 | ............... 514/237.5 |
| WO | 99/18967 | * 4/1999 | ............... 514/237.5 |

* cited by examiner

*Primary Examiner*—James H Reamer
(74) *Attorney, Agent, or Firm*—Gilberto M. Villacorta; Matten Muchin Zavis Rosenman; Robert W. Hahl

(57) ABSTRACT

There is described a method of treatment of a patient requiring analgesia which comprises the separate, simultaneous or sequential administration of a therapeutically effective amount of an opioid analgesic, devazepide and a surfactant.

There is also described a monophasic pharmaceutical composition comprising an amount of devazepide effective in the enhancement of opioid analgesia and a pharmaceutically acceptable surfactant.

124 Claims, No Drawings

METHOD OF TREATMENT

CROSS-REFERENCE TO RELATED APPLICATIONS

This application is a continuation-in-part of Ser. No. 10/108,659 filed Mar. 27, 2002 which is a continuation-in-part of Ser. No. 10/053,962 filed Jan. 22, 2002.

This invention relates to a novel method of treatment and a novel pharmaceutical composition related thereto.

International Patent Application No. WO 99/18967 describes pharmaceutical compositions for treating chronic and neuropathic pain which comprises an analgesic amount of an opioid and an opioid potentiating amount of a CCK antagonist. WO '967 describes the use of both CCK-A (CCK-1) antagonists and CCK-B (CCK-2) antagonists, although it is described that, generally, CCK-B (CCK-2) antagonists are preferred. Moreover, page 2, lines 6 to 8 of WO '967 describes that CCK-A (CCK-1) antagonists may be suitable, but only at relatively higher dosages.

One specific CCK-A (CCK-1) antagonist which is mentioned in WO 99/18967 is devazepide (Devacade®), which is 3s-(-)-1,3-dihydro-3-(2-indolecarbonylamino)-1-methyl-5-phenyl-2H-1,4-benzodiazepin-2-one.

Devazepide is commonly administered alongside an opioid analgesic, e.g. such as morphine. However, in normal doses, the commonest side-effects of morphine and other opioid analgesics are nausea, vomiting, constipation, drowsiness, and confusion; tolerance generally develops with long-term use, but not to constipation which is the most common undesirable side effect of morphine treatment.

International Patent Application No. WO 99/18967 specifically describes a pharmaceutical formulation comprising a CCK antagonist, such as devazepide, an opioid and a biphasic carrier, comprising a glyceride derivative organic phase. This application suggests the possible use of a surfactant, especially when the formulation is in the form of an oil-in-water emulsion.

We have now surprisingly found that a method of treatment of a patient requiring analgesia which comprises administering a monophasic form of devazepide which may be prepared with a surfactant. The use of a surfactant is advantageous in that, inter alia, it improves the powder flow and/or separation properties of solid devazepide and also reduces or mitigates the undesirable side effects of opioid administration, e.g. constipation.

Thus, according to the invention we provide a method of treatment of a patient requiring analgesia which comprises the separate, simultaneous or sequential administration of a therapeutically effective amount of an opioid analgesic, devazepide and a pharmaceutically acceptable surfactant wherein the daily dosage of devazepide is up to 0.7 mg/kg/day.

The method of the invention especially provides a method as hereinbefore described wherein the devazepide and the pharmaceutically acceptable surfactant are in a monophasic form, e.g. solid or liquid form. Preferably, the devazepide and the pharmaceutically acceptable surfactant are in a monophasic form, eg a liquid form or a solid dosage form. The phrase solid dosage form may mean, for example, in tablet form or, preferably in the form of a flowable powder in a capsule. We have found that the use of a surfactant in a solid dose devazepide composition as hereinbefore described has the advantage of mitigating constipation due to the concomitant administration of an opioid analgesic, whilst also improving the physical properties of devazepide in a solid dose formulation.

Any conventionally known pharmaceutically acceptable surfactants may be used in the method of the invention. Such surfactants include, but shall not be limited to, a lipophilic surfactant, a hydrophilic surfactant or a glyceride, or combinations thereof.

When the surfactant is a hydrophilic surfactant, it may be an ionic or a non-ionic surfactant. Examples of non-ionic hydrophilic surfactants include, inter alia, alkylglucosides; alkylmaltosides; alkylthioglucosides; lauryl macrogolglycerides; polyoxyethylene alkyl ethers; polyoxyethylene alkylphenols; polyethylene glycol fatty acids esters, polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene sterols, derivatives, and analogues thereof; polyoxyethylene vegetable oils; polyoxyethylene hydrogenated vegetable oils; reaction mixtures of polyols and at least one member of the group consisting of fatty acids, glycerides, vegetable oils, hydrogenated vegetable oils, and sterols; tocopherol polyethylene glycol succinates; sugar esters; sugar ethers; sucroglycerides; and mixtures thereof.

Examples of ionic hydrophilic surfactants include, inter alia, alkyl ammonium salts, bile acids and salts, analogues, and derivatives thereof; fatty acid derivatives of amino acids, carnitines, oligopeptides, and polypeptides; glyceride derivatives of amino acids, oligopeptides, and polypeptides; acyl lactylates; mono-, diacetylated tartaric acid esters of mono-, diglycerides; succinoylated monoglycerides; citric acid esters of mono-, diglycerides; alginate salts; propylene glycol alginate; lecithins and hydrogenated lecithins; lysolecithin and hydrogenated lysolecithins; lysophospholipids and derivatives thereof, phospholipids and derivatives thereof; salts of alkylsulphates; salts of fatty acids; sodium docusate; and mixtures thereof.

Examples of lipophilic surfactants include, inter alit, alcohols; polyoxyethylene alkylethers; fatty acids, bile acids; glycerol fatty acid esters; acetylated glycerol fatty acid esters; lower alcohol fatty acids esters; polyethylene glycol fatty acid esters; polyethylene glycol glycerol fatty acid esters; polypropylene glycol fatty acid esters; polyoxyethylene glycerides; lactic acid derivatives of mono/diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; polyoxyethylene hydrogenated vegetable oils; reaction mixtures of polyols and at least one member of the group consisting of fatty acids, glycerides, vegetable oils, hydrogenated vegetable oils, and sterols; and mixtures thereof.

Examples of glycerides include mono-, di- or triglycerides. Such triglycerides include, inter alia, vegetable oils, fish oils, animal fats, hydrogenated vegetable oils, partially hydrogenated vegetable oils, synthetic triglycerides, modified triglycerides, fractionated triglycerides, and mixtures thereof.

In an especially preferred embodiment of the invention the surfactant will be capable of improving powder flow of devazepide and may be known to be a therapeutically effective laxative and/or stool softener. Such laxatives and/or stool softeners may, preferentially be ionic surfactants, especially alkyl sulphosuccinates, alkyl sulphates or alkyl ammonium salts.

Thus, in a preferred embodiment of the invention the surfactant may be selected from the group, docusate sodium (dioctyl sodium sulphosuccinate), sodium dodecyl sulphate and tetradecyltrimethyl ammonium bromide.

In a further embodiment of the invention the surfactant may also possess antimicrobial and/or antiseptic properties. Thus, for example, when the surfactant is tetradecyltrimethylammonium bromide, it may, preferentially, be cetrimide (cetrimide is a mixture substantially comprising tetradecyltrimethyl ammonium bromide and small amounts of dodecyltrimethylammonium bromide and cetrimonium bromide).

In the most preferred embodiment of the invention the surfactant is docusate sodium.

The method of the invention may preferentially comprise the use of a composition which comprises one or more fillers. Thus, such fillers may be selected from the group lactose, mannitol, talc, magnesium stearate, sodium chloride, potassium chloride, citric acid, spray-dried lactose, hydrolysed starches, directly compressible starch, microcrystalline cellulose, cellulosics, sorbitol, sucrose, sucrose-based materials, icodextrin, calcium sulphate, dibasic calcium phosphate and dextrose. A preferred filler is starch, e.g. corn starch.

When the method of the invention comprises the use of a composition which includes a filler, the size of the devazepide and filler particles may be the same or different. However, in a preferred embodiment the sizes of the devazepide and filler particles will differ. Preferentially, the devazepide, surfactant and/or the filler may be of reduced particle size, e.g. by milling.

The devazepide, surfactant and filler may be present as an intimate mixture. However, in a preferred embodiment the filler particles may be coated with the surfactant, the coated filler and devazepide then being formed into an intimate mixture.

The method of the invention wherein the compositions, comprising devazepide, a filler and a surfactant are especially advantageous in that, inter alia, the surfactant acts to hinder or prevent separation of the devazepide and the filler. Furthermore, in one embodiment of the invention the surfactant may also have desirable laxative and/or stool softening properties.

The amount of surfactant present in the composition used in the method of the invention may vary, depending upon, inter alia, the level of devazepide present, the level of concomitant opioid analgesic administered, etc. Generally, the ratio of devazepide:surfactant may be from 5:1 to 25:1 w/w, preferably from 10:1 to 15:1 w/w, most preferably 12.5:1 w/w.

When the composition used in the method of the invention includes a filler, the composition may generally comprise devazepide and a surfactant, in the ratio as hereinbefore described, with the remainder of the composition being made up with a filler.

A preferred embodiment of the invention comprises a method wherein a composition as hereinbefore described is filled into a capsule. Any conventionally known materials may be used for the capsule, however a preferred material is gelatin.

Thus, for example, in one embodiment of the invention the composition as hereinbefore described may be made up into a capsule formulation, e.g. with a fill weight of 150 mg±5% by weight or 300 mg±5% by weight. In the one preferred embodiment, the capsule formulation may comprise 1.25 mg devazepide, 0.1 mg surfactant, e.g. docusate sodium, and 148.65 mg of a filler, e.g. corn starch. In a further preferred embodiment, the capsule formulation may comprise 2.5 mg devazepide, 0.2 mg surfactant, e.g. docusate sodium, and 297.3 mg of a filler, e.g. corn starch.

According to a further aspect of the invention we provide the use of devazepide in the manufacture of a pharmaceutical composition comprising a therapeutically effective amount of devazepide and a pharmaceutically acceptable surfactant The use of the invention is preferentially the use in the manufacture of a pharmaceutical composition wherein the composition comprises any of the aspects of the methods hereinbefore described. The use as hereinbefore described preferentially comprises the use in the manufacture of a pharmaceutical composition in monophasic form.

By the term therapeutically effective amount of devazepide we generally mean an amount of devazepide effective in the enhancement of opioid analgesia.

In the method of the invention a variety of opioids may be used. Thus, the opioid may be selected from those which are effective analgesics and particularly those which need to be administered at relatively high or increasing doses. Examples include morphine, or a salt thereof such as the sulphate, chloride or hydrochloride, or the other 1,4-hydroxymorphinan opioid analgesics such as naloxone, meperidine, butorphanol or pentazocine, or morphine-6-glucuronide, codeine, dihydrocodeine, diamorphine, dextropropoxyphene, pethidine, fentanyl, alfentanil, alphaprodine, buprenorphine, dextromoramide, diphenoxylate, dipipanone, heroin (diacetylmorphine), hydrocodone (dihydrocodeinone), hydromorphone (dihydromorphinone), levorphanol, meptazinol, methadone, metopon (methyldihydromorphinone), nalbuphine, oxycodone (dihydrohydroxycodeinone), oxymorphone (dihydrohydroxymorphinone), phenadoxone, phenazocine, remifentanil, tramadol, or a salt of any of these. The opioid used in the method of the invention may comprise any combination of the aforementioned compounds. Naloxone is also included within the definition of an opioid. Especially preferred analgesics which may be mentioned are hydromorphone, oxycodone, morphine, e.g. morphine sulphate and fentanyl. In a preferred embodiment of the invention the analgesic is morphine or morphine sulphate. In a further preferred embodiment the opioid is fentanyl or a salt thereof.

In the method of the invention the devazepide and/or the opioid may be administered using any methods conventionally known per se. Thus, such methods would include, but shall not be limited to, administration intravenously, intra-arterially, orally, intrathecally, intranasally, intrarectally, intramuscularly/subcutaneously, by inhalation and by transdermal patch. When the devazepide and/or opioid is administered intravenously, it may, for example, be as an intravenous bolus or a continuous intravenous infusion. When the devazepide and/or the opioid is administered subcutaneously, it may for example be by subcutaneous infusion. Preferably, the opioid and/or devazepide are administered intravenously or orally. Oral administration is especially preferred. In a further preferred embodiment the opioid may be administered by a transdermal patch. When a transdermal patch is used, the preferred opioid is fentanyl or a salt thereof.

Thus, in the method of the invention the daily dosage of devazepide may vary depending upon, inter alia, the weight of the patient, the method of administration, etc. In patients that are suffering serious disorders, such as cancer patients, the weight of the patient may be very low and therefore the dosage of devazepide consequentially may be low. Preferably, the daily dosage of devazepide may be from 25 µg/kg/day to 0.7 mg/kg/day, more preferably from 50 µg/kg/day to 0.5 mg/kg/day. For oral administration the daily dosage of devazepide may be from 0.07 mg/kg/day to 0.7 mg/kg/day, preferably 0.07 mg/kg/day to 0.29 mg/kg/day. For intravenous administration the dosage of devazepide is preferably 50 µg/kg/day to 0.5 mg/kg/day.

Thus, the expected daily dose of surfactant, which may optionally have laxative and/or stool softening properties, may be up to 0.056 mg/kg/day. Thus, dependant upon the patient, the daily dosage of surfactant may be from 0.4 mg to 1.6 mg, preferably 0.8 mg. Most preferably, the surfactant will be one which posses both laxative and stool softening properties.

In the method of the invention the dosage of the opioid analgesic administered may vary depending upon, inter alia, the nature of the opioid analgesic, the weight of the patient, the method of administration, etc. Thus, for example, the dosage of, e.g. an opioid, such as morphine, may be from 5 to 2000 mg daily. A particular dosage which may be mentioned is from 10 to 240 mg daily. A daily dosage of morphine may be from 5 to 100 mg or occasionally up to 500 mg.

According to a yet further aspect of the invention we provide a monophasic pharmaceutical composition comprising an amount of devazepide effective in the enhancement of opioid analgesia and a pharmaceutically acceptable surfactant.

Preferably, the devazepide and the pharmaceutically acceptable surfactant are in a solid dosage form. The phrase solid dosage form may mean, for example, in tablet form or, preferably in the form of a flowable powder in a capsule.

The composition of this aspect of the invention is preferentially a composition which comprises any of the aspects of the methods hereinbefore descried.

The devazepide used in the method and/or the composition of the invention is the S enantiomer, preferentially, the S enantiomer wherein the level of R enantiomer, which may be present as an impurity, is not greater than 1.5% w/w.

What is claimed is:

1. A method of treatment of a patient requiring analgesia which comprises the separate, simultaneous or sequential administration of a therapeutically effective amount of an opioid analgesic, devazepide and a pharmaceutically acceptable surfactant wherein the devazepide and surfactant relieve constipation and the daily dosage of devazepide is up to 0.7 mg/kg/day.

2. A method of treatment of a patient undergoing opioid analgesic therapy which comprises the administration of a pharmaceutical composition comprising a therapeutically effective amount of devazepide and a pharmaceutically acceptable surfactant wherein the devazepide and surfactant relieve constipation and the daily dosage of devazepide is up to 0.7 mg/kg/day.

3. method of treatment according to claims 1 or 2 characterised in that the devazepide and surfactant are presented as a monophasic form pharmaceutical composition.

4. A method according to claims 1 or 2 characterised in that the daily dosage of devazepide is from 25 µg/kg/day to 0.7 mg/kg/day.

5. A method according to claim 4 characterised in that the daily dosage of devazepide is from 50 µg 1 kg/day to 0.5 mg/kg/day.

6. A monophasic pharmaceutical composition according to claim 3 characterised in that the composition is in a liquid form.

7. A method of treatment according to claim 3 characterised in that the devazepide and surfactant are in a solid dosage form.

8. A method of treatment according to claim 7 characterised in that the devazepide and surfactant are in a tablet form.

9. A method of treatment according to claim 7 characterised in that the devazepide and surfactant are in the form of a flowable powder in a capsule.

10. A method according to claims 1 or 2 characterised in that the method of delivery of the devazepide and/or the opioid is selected from the group, administration intravenously, intra-arterially, orally, intrathecally, intranasally, intrarectally, intramuscularly/subcutaneously, by inhalation and by transdermal patch.

11. A method according to claim 10 characterised in that the devazepide and/or the opioid is administered intravenously.

12. A method according to claim 11 characterised in that the intravenous administration is by intravenous bolus or a continuous intravenous infusion.

13. A method according to claim 10 characterised in that the devazepide and/or the opioid is administered subcutaneously.

14. A method according to claim 13 characterised in that the subcutaneous administration is as a subcutaneous infusion.

15. A method according to claim 10 characterised in that the devazepide and/or the opioid is administered orally.

16. A method according to claim 10 characterised in that the devazepide is administered orally.

17. A method according to claim 11 characterised in that the opioid is administered intravenously and the devazepide is administered intravenously.

18. A method according to claim 15 characterised in that the opioid is administered orally and the devazepide is administered orally.

19. A method according to claim 10 characterised in that the opioid is administered by intravenous administration or oral administration.

20. A method according to claim 10 characterised in that the opioid is administered by transdermal patch.

21. A method according to claim 16 characterised in that for oral administration the daily dosage of devazepide is from 0.07 mg/kg/day to 0.7 mg/kg/day.

22. A method according to claim 21 characterised in that for oral administration the daily dosage of devazepide is from 0.07 mg/kg/day to 0.29 mg/kg/day.

23. A method according to claim 11 characterised in that for intravenous administration the dosage of devazepide is 50 µg/kg/day to 0.5 mg/kg/day.

24. A method according to claims 1 or 2 characterised in that the opioid is selected from the group morphine, or a salt thereof such as the sulphate, chloride or hydrochloride, or the other 1,4-hydroxymorphinan opioid analgesics such as naloxone, meperidine, butorphanol or pentazocine, or morphine-6-glucuronide, codeine, dihydrocodeine, diamorphine, dextropropoxyphene, pethidine, fentanyl, alfentanil, alphaprodine, buprenorphine, dextromoramide, diphenoxylate, dipipanone, heroin (diacetylmorphine), hydrocodone (dihydrocodeinone), hydromorphone (dihydromorphinone), levorphanol, meptazinol, methadone, metopon (methyldihydromorphinone), nalbuphine, oxycodone (dihydrohydroxycodeinone), oxymorphone (dihydrohydroxymorphinone), phenadoxone, phenazocine, remifentanil, tramadol, or a salt of any of these or any combination of the aforementioned compounds.

25. A method according to claim 24 characterised in that the opioid is selected from the group hydromorphone, oxycodone, morphine, and fentanyl, and salts thereof.

26. A method according to claim 25 characterised in that the opioid is morphine or morphine sulphate.

27. A method according to claim 25 characterised in that the opioid is fentanyl, or a salt thereof.

28. A method according to claims 1 or 2 characterised in that the daily dose of surfactant is up to 0.056 mg/kg/day.

29. A method according to claims 1 or 2 characterised in that the daily dose of surfactant is from 0.4 mg to 1.6 mg per day.

30. A method according to claims 1 or 2 characterised in that the dosage of an opioid is from 5 to 2000 mg daily.

31. A method according to claim 30 characterised in that the dosage of the opioid is from 10 to 240 mg daily.

32. A method according to claim 31 characterised in that the daily dosage of the opioid is from 5 to 100 mg daily.

33. A method according to claims 1 or 2 characterised in that the devazepide used in the method of the invention is substantially the S enantiomer.

34. A method according to claim 33 characterised in that the level of R enantiomer, which may be present as an impurity, is not beater than 1.5% w/w.

35. A method according to claim 1 or 2 characterised in that the surfactant is a lipophilic surfactant, a hydrophilic or a glyceride, or combinations thereof.

36. A method according to claim 35 characterised in that the surfactant is a hydrophilic surfactant.

37. A method according to claim 36 characterised in that the hydrophilic surfactant is an ionic or a non-ionic surfactant.

38. A method according to claim 37 characterised in that the hydrophilic surfactant is a non-ionic surfactant selected from the group alkylglucosides; alkylmaltosides;

alkyithioglucosides; lauryl macrogoiglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene sterols, derivatives, and analogues thereof; polyoxyethylene vegetable oils; polyoxyethylene hydrogenated vegetable oils; reaction mixtures of polyols and at least one member of the group consisting of fatty acids, glycerides, vegetable oils, hydrogenated vegetable oils, and sterols;

tocopherol polyethylene glycol succinates; sugar esters; sugar ethers; sucroglycerides; and mixtures thereof.

39. A method according to claim 37 characterised in that the hydrophilic surfactant is an ionic surfactant selected from the group alkyl ammonium salts; bile acids and salts, analogues, and derivatives thereof; fatty acid derivatives of amino acids, carnitines, oligopeptides, and polypeptides; glyceride derivatives of amino acids, oligopeptides, and polypeptides; acyl lactylates; mono-, diacetylated tartaric acid esters of mono-, diglycerides; succinoylated monoglycerides; citric acid esters of mono-, diglycerides; alginate salts; propylene glycol alginate; lecithins and hydrogenated lecithins; lysolecithin and hydrogenated lysolecithins;

lysophospholipids and derivatives thereof; phospholipids and derivatives thereof; salts of alkylsuiphates; salts of fatty acids; docusate sodium; and mixtures thereof.

40. A method according to claim 35 characterised in that the surfactant is a lipophilic surfactant.

41. A method according to claim 40 characterised in that the lipophilic surfactant is selected from the group alcohols; polyoxyethylene alkylethers; fatty acids; bile acids; glycerol fatty acid esters; acetylated glycerol fatty acid esters; lower alcohol fatty acids esters;

polyethylene glycol fatty acid esters; polyethylene glycol glycerol fatty acid esters;

polypropylene glycol fatty acid esters; polyoxyethylene glycerides; lactic acid derivatives of mono/diglycerides; propylene glycol diglycerides; sorbitan fatty acid esters; polyoxyethylene sorbitan fatty acid esters; polyoxyethylenepolyoxypropylene block copolymers; transestenfied vegetable oils; sterols; sterol derivatives; sugar esters; sugar ethers; sucroglycerides;

polyoxyethylene vegetable oils; polyoxyethylene hydrogenated vegetable oils; reaction mixtures of polyols and at least one member of the group consisting of fatty acids, glycerides, vegetable oils, hydrogenated vegetable oils, and sterols; and mixtures thereof.

42. A method according to claim 41 characterised in that the surfactant is a glyceride.

43. A method according to claim 42 characterised in that the triglyceride is selected from the group vegetable oils, fish oils, animal fats, hydrogenated vegetable oils, partially hydrogenated vegetable oils, synthetic triglycerides, modified triglycerides, fractionated triglycerides, and mixtures thereof.

44. A method according to claims 1 or 2 characterised in that the surfactant is a therapeutically effective laxative and/or stool softener.

45. A method according to claims 1 or 2 characterised in that the surfactant is selected from the group alkyl sulphosuccinates, alkyl sulphates or alkyl ammonium salts, 46. A method according to claim 45 characterised in that the surfactant is selected from the group, docusate sodium (dioctyl sodium sulphosuccinate), sodium dodecyl sulphate and tetradecyltrimethyl ammonium bromide.

47. A method according to claims 1 or 2 characterised in that the surfactant also possesses antimicrobial and/or antiseptic properties.

48. A method according to claim 47 characterised in that the surfactant is cetrimide.

49. A method according to claim 46 characterised in that the surfactant is docusate sodium.

50. A method according to claims 1 or 2 characterised in that the composition comprises one or more fillers.

51. A method according to claim 50 characterised in that the filler particles are coated with surfactant, the coated filler and devazepide then being formed into an intimate mixture.

52. A method according to claim 50 characterised in that the filler is selected from the group lactose, mannitol, talc, magnesium stearate, sodium chloride, potassium chloride, citric acid, spray-dried lactose, hydrolysed starches, starch, microcrystalline cellulose, cellulosics, sorbitol, sucrose, sucrose-based materials, icodextrin, calcium sulphate, dibasic calcium phosphate and dextrose and mixtures thereof.

53. A method according to claim 52 characterised in that the filler is starch.

54. A method according to claim 53 characterised in that the starch is corn starch.

55. A method according to claim 50 characterised in that the size of the devazepide particles and the filler particles are substantially different.

56. A method according to claims 1 or 2 characterised in that the ratio of devazepide:surfactant is from 5:1 to 25:1 w/w.

57. A method according to claim 49 characterised in that the composition comprises devazepide and a surfactant with the remainder of the composition being made up with a filler.

58. A method according to claim 56 characterised in that the composition comprises 1.25 mg devazepide, 0.1 mg surfactant and 148.65 mg of a filler.

59. A method according to claim 57 characterised in that the composition comprises 1.25 mg devazepide, 0.1 mg docusate sodium and 148.65 mg of corn starch.

60. A method according to claim 56 characterised in that the composition comprises is 2.5 mg devazepide, 0.2 mg surfactant and 297.3 mg of a filler.

61. A method according to claim 59 characterised in that the composition comprises 2.5 mg devazepide, 0.2 mg docusate sodium and 297.3 mg corn starch.

62. A method according to claims 1, 2 or 49 characterised in that the composition is filled into a capsule.

63. A method according to claim 61 characterised in that the capsule is a gelatin capsule.

64. A monophasic pharmaceutical composition comprising a therapeutically effective amount of devazepide and a pharmaceutically acceptable surfactant wherein the devazepide and surfactant relieve constipation and the daily dosage of devazepide is up to 0.7 mg/kg/day.

65. A monophasic pharmaceutical composition according to claim 64 characterised in that the daily dosage of devazepide is from 25 µg/kg/day to 0.7 mg/kg/day.

66. A monophasic pharmaceutical composition according to claim 65 characterised in that the daily dosage of devazepide is from 50 µg/kg/day to 0.5 mg/kg/day.

67. A monophasic pharmaceutical composition according to claim 64 characterised in that the composition is in a liquid form.

68. A monophasic pharmaceutical composition according to claim 64 characterised in that the composition is in a solid dosage form.

69. A monophasic pharmaceutical composition according to claim 68 characterised in that the composition is in the form of a tablet.

70. A monophasic pharmaceutical composition according to claim 68 characterised in that the composition is in the form of a flowable powder in a capsule.

71. A monophasic pharmaceutical composition according to claim 64 characterised in that the composition is adapted for the separate, simultaneous or sequential administration with a therapeutically effective amount of an opioid analgesic.

72. A monophasic pharmaceutical composition according to claim 64 characterised in that the composition is adapted to be administered intravenously, intra-arterially, orally, intrathecally, intranasally, intrarectally, intramuscularly/subcutaneously, by inhalation or by transdermal patch.

73. A monophasic pharmaceutical composition according to claim 72 characterised in that the devazepide and/or the opioid is adapted to be administered intravenously.

74. A monophasic pharmaceutical composition according to claim 73 characterised in that the intravenous administration is by intravenous bolus or a continuous intravenous infusion.

75. A monophasic pharmaceutical composition according to claim 72 characterised in that the devazepide and/or the opioid is adapted to be administered subcutaneously.

76. A monophasic pharmaceutical composition according to claim 75 characterised in that the subcutaneous administration is as a subcutaneous infusion.

77. A monophasic pharmaceutical composition according to claim 72 characterised in that the devazepide and/or the opioid is adapted to be administered orally.

78. A monophasic pharmaceutical composition according to claim 72 characterised in that the devazepide is administered orally.

79. A monophasic pharmaceutical composition according to claim 73 characterised in that the opioid is administered intravenously and the devazepide is administered intravenously.

80. A monophasic pharmaceutical composition according to claim 77 characterised in that the opioid is administered orally and the devazepide is administered orally.

81. A monophasic pharmaceutical composition according to claim 72 characterised in that the opioid is administered by intravenous administration or oral administration.

82. A monophasic pharmaceutical composition according to claim 72 characterised in that the opioid is administered by transdermal patch.

83. A monophasic pharmaceutical composition according to claim 72 characterised in that for oral administration the daily dosage of devazepide is from 0.07 mg/kg/day to 0.7 mg/kg/day.

84. A monophasic pharmaceutical composition according to claim 83 characterised in that for oral administration the daily dosage of devazepide is from 0.07 mg/kg/day to 0.29 mg/kg/day.

85. A monophasic pharmaceutical composition according to claim 84 characterised in that for intravenous administration the dosage of devazepide is 50 µg/kg/day to 0.5 mg/kg/day.

86. A monophasic pharmaceutical composition according to claim 64 characterised in that the opioid is selected from the group morphine, or a salt thereof such as the sulphate, chloride or hydrochloride, or the other 1,4-hydroxymorphinan opioid analgesics such as naloxone, meperidine, butorphanol or pentazocine, or morphine-6-glucuronide, codeine, dihydrocodeine, diamorphine, dextropropoxyphene, pethidine, fentanyl, alfentanil, alphaprodine, buprenorphine, dextromoramide, diphenoxylate, dipipanone, heroin (diacetylmorphine), hydrocodone (dihydrocodeinone), hydromorphone (dihydromorphinone), levorphanol, meptazinol, methadone, metopon (methyldihydromorphinone), nalbuphine, oxycodone (dihydrohydroxycodeinone), oxymorphone (dihydrohydroxymorphinone), phenadoxone, phenazocine, remifentanil, tramadol, or a salt of any of these, or any combination of the aforementioned compounds.

87. A monophasic pharmaceutical composition according to claim 86 characterised in that the opioid is selected from the group hydromorphone, oxycodone, morphine and fentanyl, or a salt thereof.

88. A monophasic pharmaceutical composition according to claim 87 characterised that the opioid is morphine or morphine sulphate.

89. A monophasic pharmaceutical composition according to claim 87 characterised in that the opioid is fentanyl, or a salt thereof.

90. A monophasic pharmaceutical composition according to claim 64 characterised in that the daily dose of surfactant is up to 0.056 mg/kg/day.

91. A monophasic pharmaceutical composition according to claim 64 characterised in that the daily dose of surfactant is from 0.4 mg to 1.6 mg per day.

92. A monophasic pharmaceutical composition according to claim 64 characterised in that the dosage of an opioid is from 5 to 2000 mg daily.

93. A monophasic pharmaceutical composition according to claim 92 characterised in that the dosage of the opioid is from 10 to 240 mg daily.

94. A monophasic pharmaceutical composition according to claim 93 characterised in that the daily dosage of the opioid is from 5 to 100 mg daily.

95. A monophasic pharmaceutical composition according to claim 64 characterised in that the devazepide is substantially the S enantiomer.

96. A monophasic pharmaceutical composition according to claim 95 characterised in that the level of R enantiomer, which may be present as an impurity, is not greater than 1.5% w/w.

97. A monophasic pharmaceutical composition according to claim 64 characterised in that the surfactant is a lipophilic surfactant, a hydrophilic or a glyceride, or combinations thereof.

98. A monophasic pharmaceutical composition according to claim 97 characterised in that the surfactant is a hydrophilic surfactant.

99. A monophasic pharmaceutical composition according to claim 98 characterised in that the hydrophilic surfactant is an ionic or a non-ionic surfactant.

100. A monophasic pharmaceutical composition according to claim 99 characterised in that the hydrophilic surfactant is a non-ionic surfactant selected from the group alkylglucosides; alkymaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene sterols, derivatives, and analogues thereof; polyoxyethylene vegetable oils; polyoxyethylene hydrogenated vegetable oils; reaction mixtures of polyols and at least one member of the group consisting of fatty acids, glycerides, vegetable oils, hydrogenated vegetable oils, and sterols; tocopherol polyethylene glycol succinates; sugar esters; sugar ethers; sucroglycerides; and mixtures thereof.

101. A monophasic pharmaceutical composition according to claim 99 characterised in that the hydrophilic surfactant is an ionic surfactant selected from the group alkyl ammonium salts; bile acids and salts, analogues, and derivatives thereof; fatty acid derivatives of amino acids, carnitines, oligopeptides, and polypeptides; glyceride derivatives of amino acids, oligopeptides, and polypeptides; acyl lactylates; mono-, diacetylated tartaric acid esters of mono-, diglycerides; succinoylated monoglycerides; citric acid esters of mono-, diglycerides; alginate salts; propylene glycol alginate; lecithins and hydrogenated lecithins; lysolecithin and hydrogenated lysolecithins; lysophospholipids and derivatives thereof, phospholipids and derivatives thereof; salts of alkylsulphates; salts of fatty acids; docusate sodium; and mixtures thereof.

102. A monophasic pharmaceutical composition according to claim 97 characterised in that the surfactant is a lipophilic surfactant.

103. A monophasic pharmaceutical composition according to claim 102 characterised in that the lipophilic surfactant is selected from the group alcohols; polyoxyethylene alkylethers; fatty acids; bile acids; glycerol fatty acid esters; acetylated glycerol fatty acid esters; lower alcohol fatty acids esters; polyethylene glycol fatty acid esters; polyethylene glycol glycerol fatty acid esters; polypropylene glycol fatty acid esters; polyoxyethylene glycerides; lactic acid derivatives of mono/diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; polyoxyethylene hydrogenated vegetable oils; reaction mixtures of polyols and at least one member of the group consisting of fatty acids, glycerides, vegetable oils, hydrogenated vegetable oils, and sterols; and mixtures thereof.

104. A monophasic pharmaceutical composition according to claim 97 characterised in that the surfactant is a glyceride.

105. A monophasic pharmaceutical composition according to claim 104 characterised in that the triglyceride is selected from the group vegetable oils, fish oils, animal fats, hydrogenated vegetable oils, partially hydrogenated vegetable oils, synthetic triglycerides, modified triglycerides, fractionated triglycerides, and mixtures thereof.

106. A monophasic pharmaceutical composition according to claim 64 characterised in that the surfactant is a therapeutically effective surfactant.

107. A monophasic pharmaceutical composition according to claim 64 characterised in that the surfactant is selected from the group alkyl sulphosuccinates, alkyl sulphates or alkyl ammonium salts.

108. A monophasic pharmaceutical composition according to claim 107 characterised in that the surfactant is selected from the group, docusate sodium (dioctyl sodium sulphosuccinate), sodium dodecyl sulphate and tetradecyltrimethyl ammonium bromide.

109. A monophasic pharmaceutical composition according to claim 64 characterised in that the surfactant also possesses antimicrobial and/or antiseptic properties.

110. A monophasic pharmaceutical composition according to claim 109 characterised in that the surfactant is cetrimide.

111. A monophasic pharmaceutical composition according to claim 108 characterised in that the surfactant is docusate sodium.

112. A monophasic pharmaceutical composition according to claim 64 characterised in that the composition comprises one or more fillers.

113. A monophasic pharmaceutical composition according to claim 112 characterised in that the filler particles are coated with the surfactant, the coated filler and devazepide then being formed into an intimate mixture.

114. A monophasic pharmaceutical composition according to claim 112 characterised in that the filler is selected from the group lactose, mannitol, talc, magnesium stearate, sodium chloride, potassium chloride, citric acid, spray-dried lactose, hydrolysed starches, starch, microcrystalline cellulose, cellulosics, sorbitol, sucrose, sucrose-based materials, icodextrin, calcium sulphate, dibasic calcium phosphate and dextrose and mixtures thereof.

115. A monophasic pharmaceutical composition according to claim 114 characterised in that the filler is starch.

116. A monophasic pharmaceutical composition according to claim 115 characterised in that the starch is corn starch.

117. A monophasic pharmaceutical composition according to claim 112 characterised in that the size of the devazepide particles and the filler particles are different.

118. A monophasic pharmaceutical composition according to claim 64 characterised in that the ratio of devazepide: surfactant is from 5:1 to 25:1 w/w.

119. A monophasic pharmaceutical composition according to claim 112 characterised in that the composition comprises devazepide and a surfactant with the remainder of the composition being made up with a filler.

120. A monophasic pharmaceutical composition according to claim 119 characterised in that the composition comprises 1.25 mg devazepide, 0.1 mg surfactant and 148.65 mg of a filler.

121. A monophasic pharmaceutical composition according to claim 120 characterised in that the composition comprises 1.25 mg devazepide, 0.1 mg docusate sodium and 148.65 mg of com starch.

122. A monophasic pharmaceutical composition according to claim 119 characterised in that the composition comprises is 2.5 mg devazepide, 0.2 mg surfactant and 297.3 mg of a filler.

123. A monophasic pharmaceutical composition according to claim 122 characterised in that the composition comprises 2.5 mg devazepide, 0.2 mg docusate sodium and 297.3 mg com starch.

124. A monophasic pharmaceutical composition according to claim 64 characterised in that the composition is filled into a capsule.

* * * * *